(12) United States Patent
French et al.

(10) Patent No.: US 7,060,023 B2
(45) Date of Patent: *Jun. 13, 2006

(54) PERICARDIUM REINFORCING DEVICES AND METHODS OF USING THEM

(75) Inventors: Ronald G. French, Santa Clara, CA (US); Sunmi K. Chew, San Jose, CA (US); Hanson S. Gifford, III, Woodside, CA (US); Bernard H. Andreas, Redwood City, CA (US)

(73) Assignee: The Foundry Inc., Menlo Park, CA (US)

( * ) Notice: Subject to any disclaimer, the term of this patent is extended or adjusted under 35 U.S.C. 154(b) by 336 days.

This patent is subject to a terminal disclaimer.

(21) Appl. No.: 09/963,848

(22) Filed: Sep. 25, 2001

(65) Prior Publication Data

US 2003/0060895 A1    Mar. 27, 2003

(51) Int. Cl.
*A61F 13/00* (2006.01)

(52) U.S. Cl. .................. 600/37; 601/153; 606/151

(58) Field of Classification Search ............. 623/11.11, 623/66.1; 606/151, 153; 600/16–18, 37; 601/151–153

See application file for complete search history.

(56) References Cited

U.S. PATENT DOCUMENTS

| | | |
|---|---|---|
| 2,826,193 A | 3/1958 | Vineberg |
| 3,464,322 A | 9/1969 | Pequignot |
| 3,513,836 A | 5/1970 | Sausse |
| 3,587,567 A | 6/1971 | Schiff |
| 3,613,672 A | 10/1971 | Schiff |
| 3,983,863 A | 10/1976 | Janke et al. |
| 4,536,893 A | 8/1985 | Parravicini |
| 4,628,937 A | 12/1986 | Hess et al. |

(Continued)

FOREIGN PATENT DOCUMENTS

EP     0 370 931 A1    5/1990

(Continued)

OTHER PUBLICATIONS

Athanasuleas, C. (2001). "Surgical Anterior Ventricular Endocardial Restoration (SAVER) in the Dilated Remodeled Ventricle After Anterior Myocardial Infarction," *JACC* 37(5):1199-1209.

(Continued)

*Primary Examiner*—David J. Isabella
*Assistant Examiner*—Urmi Chattopadhyay
(74) *Attorney, Agent, or Firm*—Townsend and Townsend and Crew LLP

(57) ABSTRACT

This is a surgical device and a method of using it. In particular, the device is one for reinforcing the pericardial sac surrounding the heart to assist in the treatment of congestive heart failure. The device, generically, is an enclosure having an interior and an exterior. The interior surface is made in such a way that it tends not to or does not form adhesions with or accept ingrowth with the myocardial tissue of the epicardium. The exterior surface of the device, in contrast, is adapted to adhere to or to ingrow with or otherwise attach sufficiently to the pericardium so that it reinforces that membrane or structure. The nature of the device is that it tends not to allow the pericardium to expand further with time. The device, after complete deployment, should envelope some measure of pericardial fluid in its interior separating it from the epicardial surface. This device helps to prevent further declination of the heart during congestive heart failure. The device is preferably introduced into the pericardial space and into the inner surface of the pericardium using transcutaneous or minimally invasive techniques.

90 Claims, 14 Drawing Sheets

U.S. PATENT DOCUMENTS

| | | |
|---|---|---|
| 4,690,134 A | 9/1987 | Snyders |
| 4,827,932 A | 5/1989 | Ideker et al. |
| 4,936,857 A | 6/1990 | Kulik |
| 4,957,477 A | 9/1990 | Lundbäck |
| 4,972,300 A | 11/1990 | Beisswanger et al. |
| 4,973,300 A | 11/1990 | Wright |
| 5,098,369 A | 3/1992 | Heilman et al. |
| 5,119,804 A | 6/1992 | Anstadt |
| 5,131,905 A | 7/1992 | Grooters |
| 5,131,907 A * | 7/1992 | Williams et al. ............... 600/36 |
| 5,256,132 A | 10/1993 | Snyders |
| 5,336,254 A | 8/1994 | Brennen et al. |
| 5,383,840 A | 1/1995 | Heilman et al. |
| 5,603,337 A | 2/1997 | Jarvik |
| 5,643,172 A | 7/1997 | Kung et al. |
| 5,702,343 A | 12/1997 | Alferness |
| 5,713,954 A | 2/1998 | Rosenberg et al. |
| 5,800,528 A | 9/1998 | Lederman et al. |
| 5,897,587 A * | 4/1999 | Martakos et al. .......... 623/1.13 |
| 5,900,528 A | 5/1999 | Berquist |
| 5,961,440 A | 10/1999 | Schweich, Jr. et al. |
| 6,037,366 A | 3/2000 | Krall et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferness |
| 6,085,784 A | 7/2000 | Bloom et al. |
| 6,095,968 A * | 8/2000 | Snyders ....................... 600/16 |
| 6,109,972 A | 8/2000 | Leinonen et al. |
| 6,110,100 A | 8/2000 | Talpade |
| 6,123,662 A | 9/2000 | Alferness et al. |
| 6,126,590 A | 10/2000 | Alfereness |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,169,922 B1 | 1/2001 | Alferness et al. |
| 6,174,279 B1 | 1/2001 | Girard |
| 6,183,411 B1 | 2/2001 | Mortier et al. |
| 6,190,408 B1 | 2/2001 | Melvin |
| 6,193,648 B1 | 2/2001 | Krueger |
| 6,210,432 B1 | 4/2001 | Solem et al. |
| 6,224,540 B1 | 5/2001 | Lederman et al. |
| 6,230,714 B1 | 5/2001 | Alferness et al. |
| 6,231,602 B1 | 5/2001 | Carpentier et al. |
| 6,234,960 B1 | 5/2001 | Aboul-Hosn et al. |
| 6,237,607 B1 | 5/2001 | Vanney et al. |
| 6,241,654 B1 | 6/2001 | Alferness |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,264,645 B1 | 7/2001 | Jonkman |
| 6,293,906 B1 | 9/2001 | Vanden Hoek et al. |
| 6,695,769 B1 * | 2/2004 | French et al. ................. 600/37 |
| 2003/0088149 A1 * | 5/2003 | Raman et al. ................ 600/37 |

FOREIGN PATENT DOCUMENTS

| | | |
|---|---|---|
| FR | 2 645 739 | 10/1990 |
| GB | 2 115 287 A | 9/1983 |
| JP | 2-271829 | 6/1990 |
| SU | 1009457 A | 4/1983 |
| SU | 1734767 A1 | 5/1992 |
| WO | WO 00/44287 | 8/2000 |
| WO | WO 01/67985 A1 | 9/2001 |

OTHER PUBLICATIONS

Comedicus, Inc. The Perducer™ Brand Pericardiocentesis Device (total pages 4).

Mussivand, T. (1999). "Mechanical Circulatory Devices for the Treatment of Heart Failure," *J. Card. Surg*, 13:218-228.

* cited by examiner

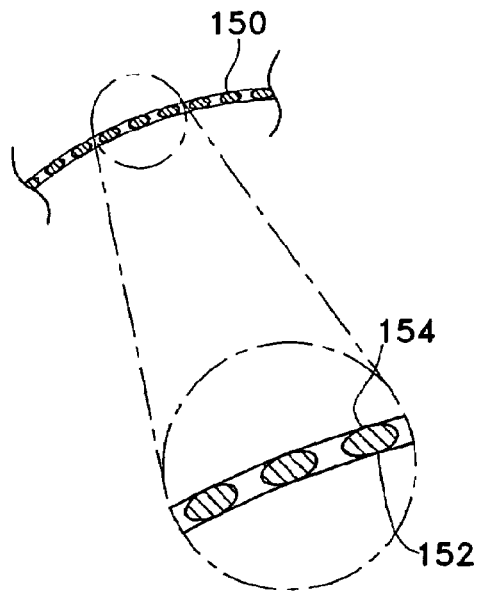
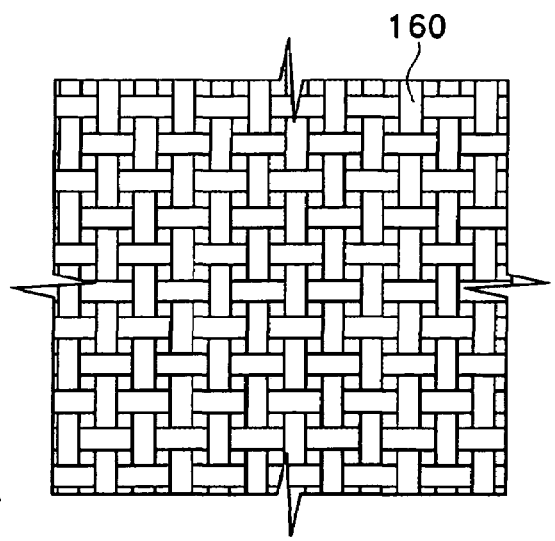
Fig. 3A     Fig. 3B
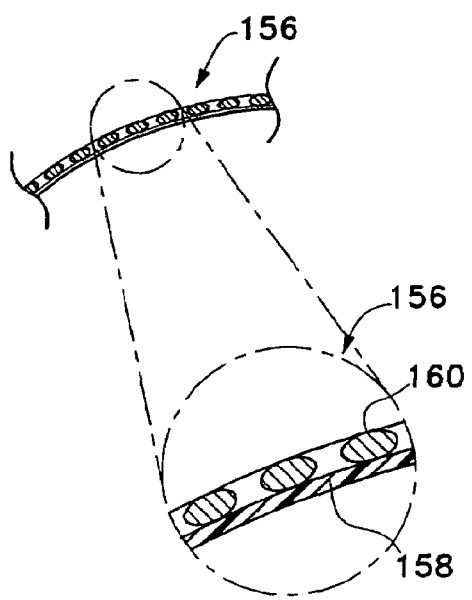
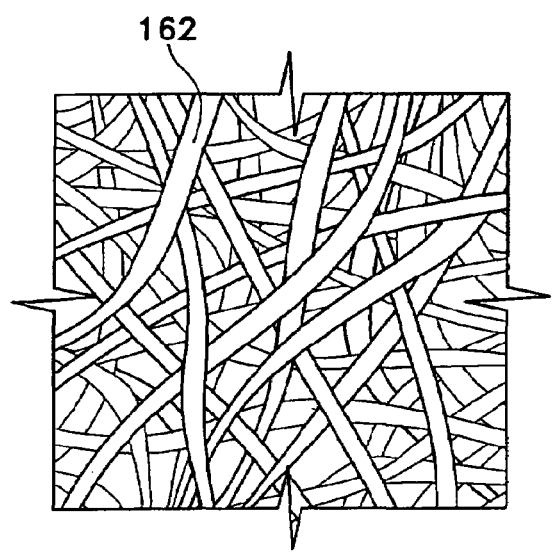
Fig. 4A     Fig. 4B

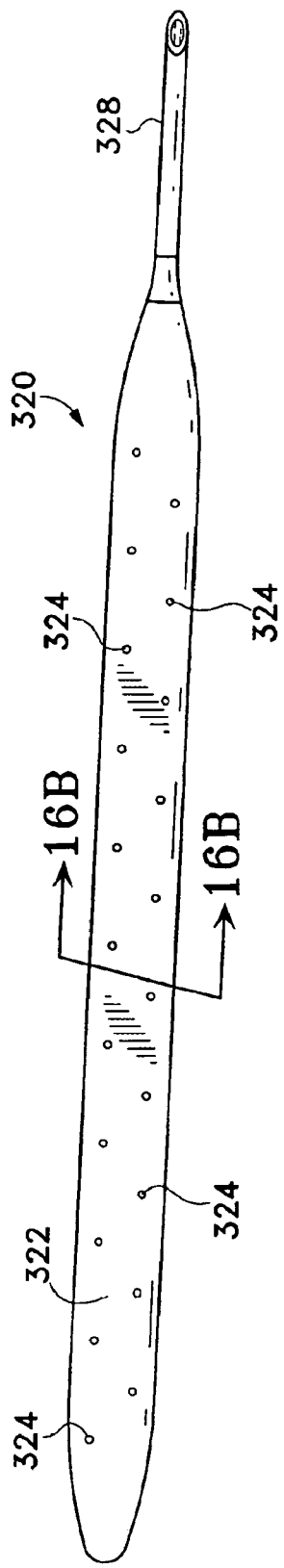
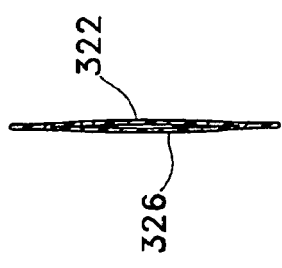
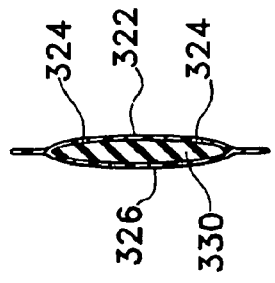
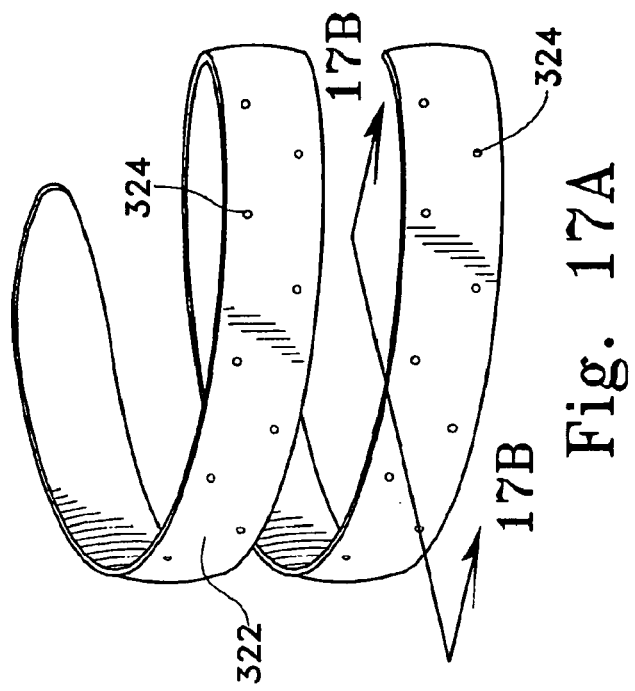
Fig. 16A
Fig. 16B
Fig. 17A
Fig. 17B

PERICARDIUM REINFORCING DEVICES AND METHODS OF USING THEM

FIELD OF THE INVENTION

This invention relates to surgical devices and to methods of using them. In particular, the device is one for reinforcing the pericardial sac surrounding the heart to assist in the treatment of congestive heart failure. The device, generically, is an enclosure having an interior and an exterior. The interior surface is made in such a way that it tends not to or does not form adhesions with or accept ingrowth with the myocardial tissue of the epicardium. The exterior surface of the device, in contrast, is adapted to adhere to or to ingrow with or otherwise to attach sufficiently to the pericardium so that it reinforces that membrane or structure. The nature of the device is that it tends not to allow the pericardium to expand further with time. The device, after complete deployment, desirably envelopes some measure of pericardial fluid in its interior separating it from the epicardial surface. This device helps to prevent further declination of the condition of the heart during the course of congestive heart failure. The device is preferably introduced into the pericardial space and onto the inner surface of the pericardium using transcutaneous or minimally invasive techniques.

BACKGROUND OF THE INVENTION

Congestive Heart Failure ("CHF"), or simply "Heart Failure" is a progressive path found in many forms of heart disease. In general, it is a condition in which the heart is unable to pump blood at a rate sufficient for the proper supply of nutrients to metabolizing tissues. There are many specific disease states leading to CHF, but each typically results in the dilatation of the ventricles. Various etiologies for CHF are viral and ischemic and, of course, idiopathic. Myocardial injury and chronic volume overload generally are thought to cause this course of ventricular dilatation. The typical adaptation process undertaken by the stressed heart muscle is not achieved during CHF and, instead of gaining a stronger heart muscle, the heart instead gets larger as it attempts to adapt to its increased volume load.

Chronic pressure overload causes another response mechanism to develop. Specifically, hypertrophy of the heart muscle, entailing an increase both in the size of individual muscle cells and in overall muscle mass, begins to occur. Although this response helps the heart to overcome higher pressure, it has limitations and is associated with various structural and biochemical changes that have deleterious long term effects.

Additionally, system-wide vascular constriction occurs during the course of CHF. The constriction causes blood flow to be redistributed so that certain regions and systems have a reduced blood supply, e.g., skeletal muscle, kidneys, and skin. These regions do not produce significant amounts of vasodilating metabolites. In contrast, the brain and heart have high metabolic rates and produce a greater amount of vasodilators. Consequently, the latter organs receives a higher proportion of the restricted blood supply.

Therapy for CHF is staged. Correction of a reversible causative factors is the first line of offense. Treatment of bradyarrhythmias, perhaps by use of an artificial pacemaker or by provision of an appropriate drug such as digitalis, can help alleviate CHF. CHF that continues after correction of such reversible causes is often treated with a regime of salt restriction, vasodilators, diuretics, and the like. Bed rest to increase venous return to the heart and move fluid from the periphery is often helpful. As noted above, digitalis has been an important drug for increasing cardiac output in persons with specific types of CHF. It has been used for over 200 years. Other drugs used for treatment of CHF include beta-adrenergic agonists such as norepinephrine, epinephrine, and isoproterenol. Each stimulate cardiac beta-adrenergic receptors. Dopamine and dobutamine are also used. Various diuretics and vasodilators for variously dilating both veins and arteries are used, each for slightly different reasons based on the detected manifestation of the CHF in the heart.

Few interventional or surgical pathways for alleviation of CHF are currently widely practiced. Indeed, the only permanent treatment for CHF is a heart transplant.

One surgical procedure known as cardiomyoplasty is used for early stage CHF. In that procedure, a muscle taken from the shoulder (the latissimus dorsi) is wrapped around the heart. The added muscle is paced synchronously with the ventricular systole. This procedure is highly invasive requiring a sternotomy to access the heart. Some have suggested that the benefits of the procedure are due more to remodeling from the mere placement of the shoulder muscle around the heart rather than from a muscular assistance.

There are a variety of devices that may be applied to the heart for treatment of CHF. Patents owned by Abiomed (U.S. Pat. Nos. 6,224,540; 5,800,528; 5,643,172) generally show a girdle-like device situated to provide structure to a failing heart. U.S. Patents owned by Acorn Cardiovascular, Inc. (U.S. Pat. Nos. 6,241,654; 6,230,714; 6,193,648; 6,174,279; 6,169,922; 6,165,122; 6,165,121; 6,155,972; 6,126,590; 6,123,662; 6,085,754; 6,077,218; 5,702,343) show various devices, also for treatment of CHF, which typically include a mesh sock-like device placed around the myocardial wall. U.S. Patents to Myocor, Inc. (U.S. Pat. Nos. 6,264,602; 6,261,222; 6,260,552; 6,183,411; 6,165,120; 6,165,119; 6,162,168; 6,077,214; 6,059,715; 6,050,936; 6,045,497; 5,961,440) show devices for treatment of CHF generally using components that pierce the ventricular wall.

None of the documents mentioned above appears to suggest the devices and methods provided for herein.

SUMMARY OF THE INVENTION

This invention is a device and a method for reinforcing the pericardium . Generically, it is made of at least one compliant member having an interior surface for placement adjacent to or spaced away from the epicardium and an exterior surface for attachment to the interior of a pericardium. The compliant member may be conformable in shape to at least a portion of the epicardium.

The interior surface is adapted to inhibit adhesions or attachment to the epicardium, e.g., via use of a material that does not substantially permit ingrowth with or that resists ingrowth with the epicardium. Suitable choices for materials that functionally provide such results include various lubricious material, perhaps polymeric, e.g., fluorocarbon polymers especially those selected from the group consisting of polytetrafluoroethylene, ethylene-chlorofluoroethylene, fluorinated ethylene propylene, polychlorotrifluoroethylene, polyvinylfluoride, and polyvinylidenefluoride and certain expanded polytetrafluoroethylenes (ePTFE). Other suitable lubricious polymers include those selected from the group consisting of LLDPE, LDPE, HDPE, polypropylene, and polyamides their mixtures and copolymers.

The exterior surface functionally adheres to or reacts with or ingrows with the pericardium in such a way that the resulting pericardium-implant combination is substantially reinforced compared to the previously existing pericardium.

The outer layer, for instance, may comprise a material for ingrowth into or with or for attachment to or adherence with the pericardium. The exterior surface may comprise a material that itself promotes ingrowth, e.g., polyethylene terephthalate, polyglycolic acid, polylactic acid, reconstituted collagen, poly-p-dioxanone, poly(glycolide-lactide) copolymer, poly(glycolide-trimethylene carbonate) copolymer, poly(glycolide-ε-caprolactone) copolymer, glycolide-trimethylene carbonate triblock copolymer, their block and random copolymers, mixtures, and alloys. Physical mixtures of the biodegradable polymers with other substantially non-biodegradable materials, (such as polyolefins or polyfluorocarbons) is desired to preserve to integrity of the flexible or compliant member. Particularly desirable are mixtures of biodegradable and non-bio-degradable polymeric fibers, perhaps by coweaving or other suitable manner of making an integrated fabric.

The outer surface may further comprise a material promoting endothelialization, such as an effective hyaluronate salt or one or more angiogenic materials such as are listed below. Physically, the outer surface may be an independent layer or an integrated layer, a woven or non-woven polymeric material. The attachment to the outer layer may be simply mechanical, and produced by, e.g., suturing or adhesively attaching it to the pericardium. The exterior surface may be textured to assist with ingrowth into the pericardium.

As noted above, the compliant member may comprise a separate inner member and an outer member, e.g., where at least one of the inner members and the outer members comprises a woven or non-woven fabric. They may be laminated together or with an intermediate between. In some instances, at least one of the inner members and the outer members is substantially non-porous, non-porous, or non-continuous.

It is desirable that the inventive device include an adjuster adapted for changing the compliant member size after attachment of that compliant member to the interior of the pericardium. The adjuster, for instance, may be a rotatable roller, a drawstring, a band, or the like. One preferable band variation is made up of an upper end and an apical end and has a length extending from the upper end to the apical end and where the length of the band is less than about ⅓ length of a heart to which it is applied. The band may have a length substantially matching the width of the A–V groove on that heart.

The shape of the compliant member may be that of a sack having a closed end, particularly one having a closed end and sized to be positioned only along and less than about ⅓ length of the heart when positioned from the apical end. The compliant member may be a substantially elongated member having a distal end and a proximal end and configured to be helical upon introduction into the region of the pericardium, perhaps having a lumen (in some instances expandable) extending from the proximal end at least partially to the distal end. The lumen may have at least one orifice open to the exterior surface when the device is helically configured in the region of the pericardium, perhaps to pass glue or adhesive to the pericardium side of the device. In some variations, the source of glue or adhesive also forms a component of the inventive device.

One very desirable form of the compliant member is an enclosure generally conforming in shape to at least a portion of an epicardium where the enclosure has at least one rib separated by and spaced apart by webbing. The rib may be at least one band having an upper end and an apical end and a length extending from the upper end to the apical end and having at least two open, generally opposing openings. Desirably, the wound band has a length less than about ⅓ length of a heart to which it is applied.

Preferably, the various ribs have a flexibility different than that of the webbing. The at least one rib may have the form of a generally helical member, perhaps ribbon-like in form. A "ribbon" is considered to have a width-thickness ratio greater than about two, perhaps greater than about seven. The helical member may be inflatable over at least a portion of the enclosure, perhaps incrementally inflatable along its length.

The compliant member may be made up of an enclosure generally conforming in shape to at least a portion of a pericardium and having multiple ribs extending from the upper end to the apical end. Desirably each rib may be ribbon-like. Alternatively, the ribs may each have a round cross section or may have a cross section with a width-thickness ratio of two or less. The multiple ribs may be zigzag in shape and where there are multiple zigzag ribs having substantially adjacent points, at least some of the adjacent points may be connected. At least some of the multiple ribs may be joined at the apical end.

The webbing may be of a variety of forms, e.g., a woven fabric, a woven open weave fabric, one or more ribbons extending between at least some of the multiple ribs, one or more fibers extending between at least some of the multiple ribs, an elastic material, a substantially inelastic material, or the like.

The compliant member may have a longitudinal opening extending from the upper end towards the apical end and including a plurality of looping members situated on the upper end (like loops on a kitchen curtain) deployable over a looping deployment tool. The deployment tool is preferably adapted to be removable after placement of the compliant member adjacent said pericardium and has a connector member for separation after installation. The invention, in some variations, includes the installation member.

The invention includes various procedures for reinforcing the pericardium. One procedure comprises the steps of introducing the inventive device through a pericardium wall into a pericardial space, desirably below the xiphoid process of a patient, and positioning the inventive pericardial reinforcement adjacent the pericardium. The procedure may include the step of puncturing skin beneath the xiphoid process with a needle and an introducer and passing the needle through the pericardium to the pericardial space. The steps of introducing a guidewire, removing the needle, and introducing a cannula may also be included Finally, the invention includes a modified pericardium reinforced with the compliant pericardial reinforcement devices discussed elsewhere.

BRIEF DESCRIPTION OF THE DRAWINGS

FIG. 3A shows a cross-sectional view of the compliant member making up one variation of the invention. FIG. 3B shows a side-view of the FIG. 3A material.

FIG. 4A shows a cross-sectional view of the compliant member making up one variation of the invention. FIG. 4B shows a side view of the FIG. 4A material.

FIGS. 16A, 16B, 17A, and 17B show, respectively, a side-view of a variation of the invention device employing adhesives prior to introduction into the pericardial sac, a cross section of that side view, a side view of the variation after introduction to the pericardial sac, and a cross section of that installed device.

DESCRIPTION OF THE INVENTION

As noted elsewhere, this invention has several related aspects: it is 1.) a device for reinforcing the pericardial sac that has an inner surface that tends not to adhere to the epicardium and an outer surface that adheres to, is intergrown with, or is made in some fashion to constrain expansion of some portion of the pericardium; 2.) methods of introducing the inventive reinforcing device to the operative site; and 3.) the resulting modified and reinforced pericardium having the inventive reinforcing device attached to it.

Our use of the term "compliant" and its variations are embodied in the following: in general, the inventive reinforcing device is constructed in such a way that it is sufficiently compliant to be placed in substantial contact with a portion of the inner surface of the pericardium to allow some measure of adherence between the two. This may mean that the device is flexible or that a portion of the device is flexible or that a portion of the device is comparatively stiffer than another portion or portions. The functional result is this: the device should reinforce the pericardium in such a way that over an extended period of time, the size of the combination of pericardium and the reinforcing device do not expand in a way consistent with the typical, ongoing progress of CHF. Additionally, we use the term "substantially non-elastic" not in an absolute sense, but simply to express the functional concept that during the use of the device in reinforcing the pericardium, the device is not substantially changing in size due to the pressures placed upon it by the beating of the heart. Some elasticity in a gross physical sense is perceived to be inevitable.

Figure 1:
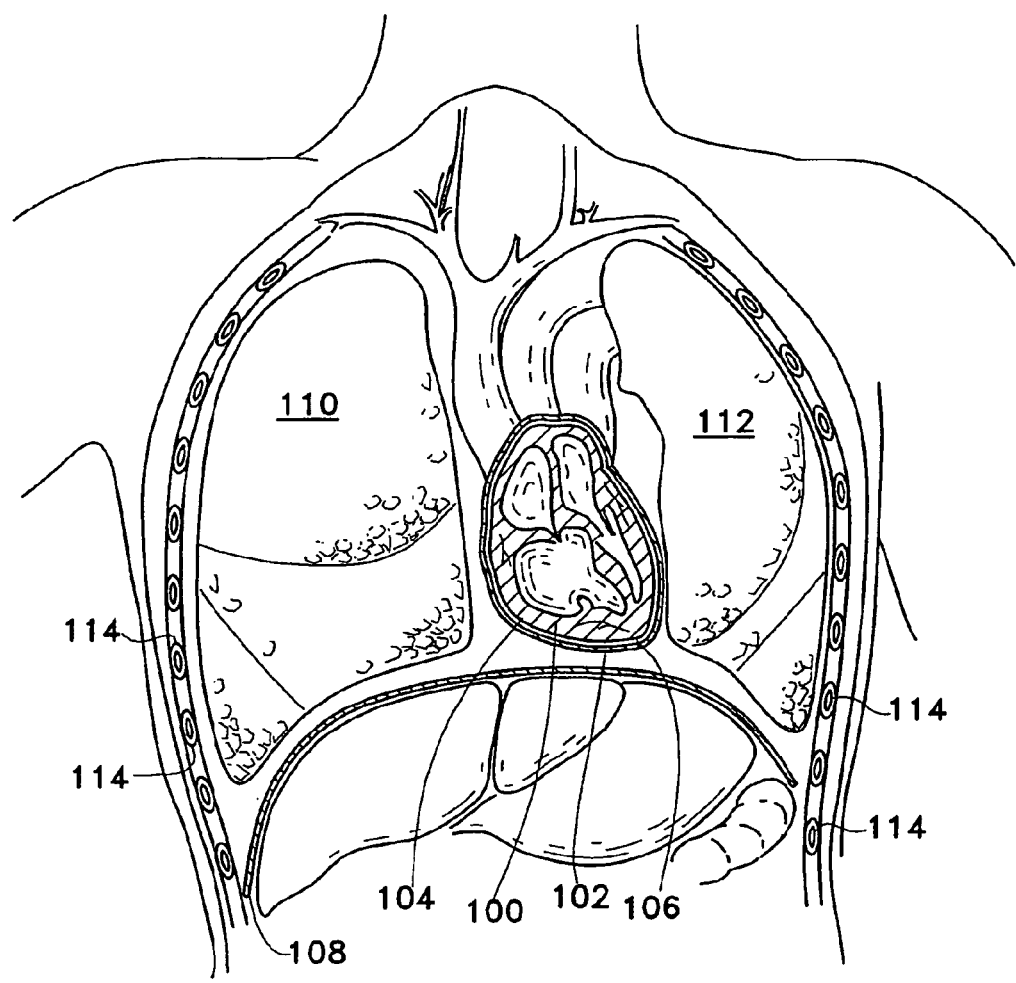
FIG. 1 is an anterior view of the heart in a human chest showing the pericardium in particular.

First, in FIG. 1, the situation of a typical human heart (100) may be seen. Of special interest here is the pericardium (102) surrounding the epicardium (104) but separated by a small barrier filled with a pericardial fluid (106). The pericardial sac or the pericardium (102) approaches the diaphragm (108) closely at the apex of the heart. In indi-viduals who are not obese, the distance from the exterior surface of the skin, through the diaphragm (108), and into the pericardial sac (102) may be as short as a couple of inches. In obese individuals, the distance can be much greater, e.g., six inches or more. As will be discussed below, this sub-xiphoid approach (a percutaneous route as described above, but below the xiphoid process not shown in FIG. 1) is highly desirable and even preferable to "cracking the chest" to introduce various implants into the cardiac space.

Also seen in FIG. 1, for reference are the lungs (110, 112) and the ribs (114). Note how far below the apex at the heart (100) the ribs extend.

Figure 2:
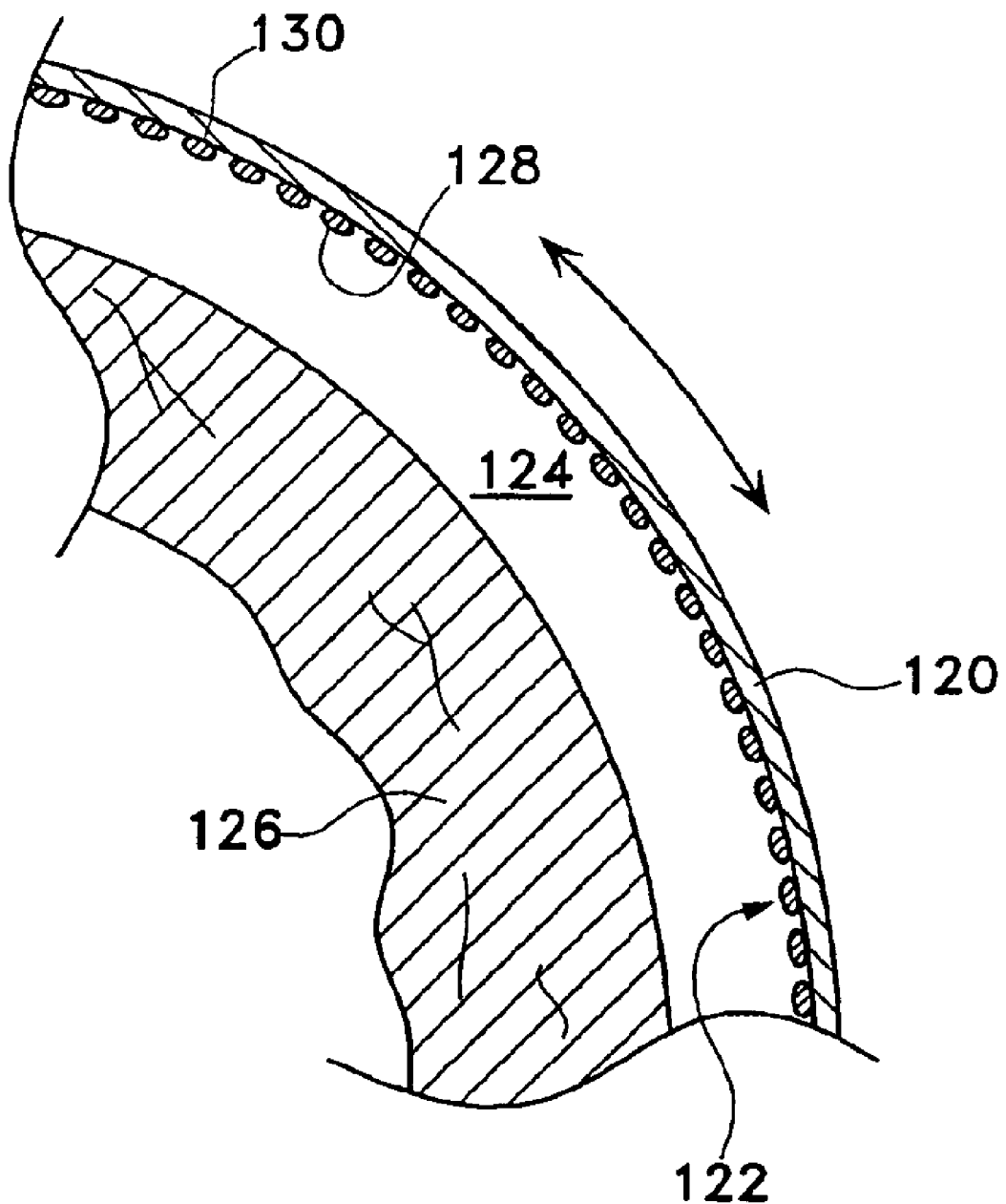
FIG. 2 is a partial cross-section of the inventive reinforcing device as deployed upon a pericardial sac and in reference to an epicardium.

FIG. 2 shows, in cross-section, a pericardium (120), reinforced by the inventive reinforcing device (122), surrounding a pericardial space (124) typically filled with a fluid, and a heart wall or epicardium (126).

The inventive device (122) has an inner surface (128) and an outer surface (130). In use, the inner surface (128) remains generally or substantially separated from the epicardium (126). In construction, the inner surface (128) is adapted not to be susceptible to adhesion to the epicardium. One way to prevent such adhesion is to configure the inner surface of a material or with a surface structure that tends not to permit adhesion with the myocardial tissue of the epicardium (126). This function may be carried out in several ways. For instance, the surface (128) confronting the epicardium (126) may be coated with a slippery material or comprise a slippery material. The device (122) may be multilayered and comprise an independent inner layer of a slippery material.

By the terms "adherence" and "adhesion," we mean that the noted specific component or region of the device is substantially locally immobile with respect to its related heart tissue. That is to say that it may be adhesively connected to the tissue, mechanically attached to the tissue, ingrown with the tissue, connected using specific mechanical connectors, or other methods of or means for preventing relative motion between the device component and the tissue wall.

FIG. 3A depicts a cross-section of a compliant member (150) having an inner non-adhering surface (152) and an outer surface (154). In this variation of the invention, the inner surface (152) is coated with a material that tends not to form adhesions with the epicardium. The non-adhering material may be sprayed on or infused into another substrate having a differing proclivity for adhesion onto heart tissue. In the absence of mechanical or chemical adhesives to the pericardial sac, the concept for this variation is simply that there exist a differential proclivity for formation of adhesion. The inner surface (152) has a comparatively lower proclivity for adhesion to cardiac tissue than does the outer surface.

Incidentally, FIGS. 3A and 3B show a typical woven fabric. The weave need not be as loose as is shown in FIG. 3B. It is also within the scope of this invention to use a random fabric or "non-woven" (as it is known in the polymer industry) for the single or multiple layers of the invention device. A non-woven material (162) is shown in FIG. 4B in another variation of the invention for another purpose, but may be coated or used as a laminate member for the inventive device.

The material used that substantially prevents adhesion to the epicardium may be one or more polymers such as polyfluorocarbons and polyolefins selected from the group consisting of polytetrafluoroethylene (PTFE or TFE), ethylene-chlorofluoroethylene (ECTFE), fluorinated ethylene propylene (FEP), polychlorotrifluoroethylene (PCTFE), polyvinylfluoride (PVF), polyvinylidenefluoride (PVDF), polyethylene (LDPE, LLDPE, and HDPE), and polypropylene. An especially desirable polymer is expanded polytetrafluoroethylene (ePTFE) that is functionally adapted to inhibit ingrowth, e.g., ePTFE having internodal differences less than about 40 microns.

Again, they may be applied as an emulsion, dispersion, or solution to another substrate material or the substrate material may instead be the substantially non-adhering material with the other side (154) treated to improve adhesion.

FIG. 4A shows a cross-section of another variation (156) of the inventive device in which the non-adherent surface (158) is a layer separate from the layer (160) adjacent the pericardium. The two layers (158) may be laminated together, if so desired. They need not be, since the function of the non-adhering side (160) is simply to prevent attachment of the epicardium to the inventive device (156). Again, both layers (158, 160) may be woven, non-woven, or a mixture as desired by the designer. FIG. 4B shows a typical "non-woven" fabric type.

Returning to FIG. 2, the surface of the reinforcing device (122) adjacent the pericardium (120) is, in some way, to be generally affixed to that pericardium. FIG. 3A shows a woven fabric member (150) having a side (154) that is adapted to biologically mesh or to ingrow with the pericardium. The adhering surface (154) may just as well be a non-woven surface.

As is shown in FIG. 4A, the adherent surface (160) may be an independent structure perhaps fixedly laminated to the generally non-adherent surface (158).

The exterior or adhering surface may comprise a material that itself promotes ingrowth, e.g., polyethylene terephthalate, polyglycolic acid, polylactic acid, reconstituted collagen, poly-p-dioxanone, poly(glycolide-lactide) copolymer, poly(glycolide-trimethylene carbonate) copolymer, poly(glycolide-ϵ-caprolactone) copolymer, glycolide-trimethylene carbonate triblock copolymer, their block and random copolymers, mixtures, and alloys. Biodegradable polymers often promote growth of endothelium and neovasculature in the body. Physical mixtures of the biodegradable polymers with other substantially non-biodegradable materials, (such as polyolefins or polyfluorocarbons) are desired to preserve the integrity of the flexible or compliant member. Particularly desirable are mixtures of biodegradable and non-biodegradable polymeric fibers, perhaps by coweaving or other suitable manner of making an integrated fabric. An especially desirable non-biodegradable polymer is expanded polytetrafluoroethylene (ePTFE) that is functionally adapted to promote ingrowth, e.g., ePTFE having internodal differences greater than about 60 microns.

Expanded polytetrafluoroethylene (ePTFE) sheets are available having an internodal distance gradient between the two sides, e.g., one side at 40 microns or less and one side having internodal distances greater than about 60 microns. Such a sheet is highly desirable.

The adhering surface of any of the variations disclosed here may be treated to enhance the biological bonding with the compliant reinforcement device. The inventive device may be adapted to promote angiogenesis adjacent the pericardium. Angiogenesis-promoting materials, particularly those that promote growth of microvasculature, whether synthetic or natural may be infused into the various components, e.g., into or onto the polymers of the inventive device adjacent the pericardium. Angiogenic materials include, e.g., collagen, fibrinogen, vitronectin, other plasma proteins, various appropriate growth factors (e.g., vascular endothelial growth factor, "VEGF"), and synthetic peptides of these and other similar proteins. Other components having a specific role may be included, e.g., genes, growth factors, biomolecules, peptides, oligonucleotides, members of the integrin family, RGD-containing sequences, oligopeptides, e.g., fibronectin, laminin, bitronectin, hyaluronic acid, silk-elastin, elastin, fibrinogen, and the like.

Other bioactive materials which may be used in the invention include, for example, pharmaceutically active compounds, proteins, oligonucleotides, ribozymes, and antisense genes. Desirable additions include vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directly against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms, and combinations thereof.

In addition, polypeptides or proteins that may be incorporated into or onto the inventive device, or whose DNA can be incorporated, include without limitation, proteins competent to induce angiogenesis, including factors such as, without limitation, acidic and basic fibroblast growth factors, vascular endothelial growth factor (including VEGF-2, VEGF-3, VEGF-A, VEGF-B, VEGF-C) hif-1 and other molecules competent to induce an upstream or downstream effect of an angiogenic factor; epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor; cell cycle inhibitors including CDK inhibitors; thymidine kinase ("TK") and other agents useful for interfering with cell proliferation, and combinations thereof.

Figure 5:
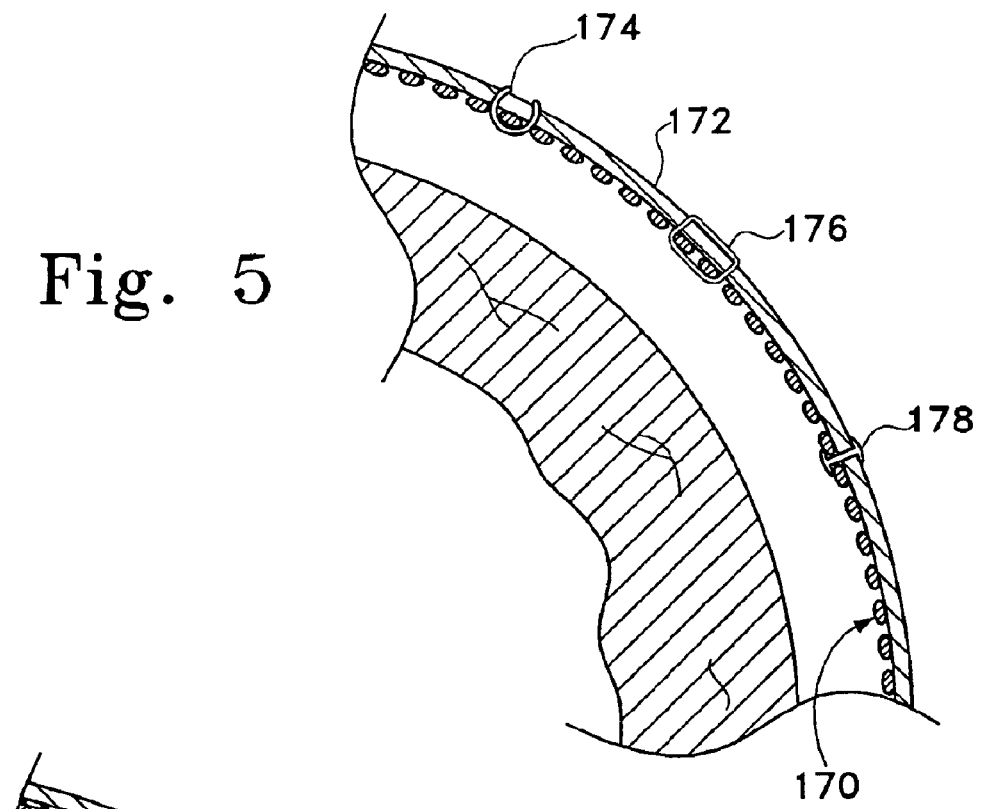
FIGS. 5 and 6 show cross-sectional views of, respectively, mechanical fasteners and adhesives in placing the inventive device on the pericardium.

In any case, it is also within the scope of this invention to utilize mechanical fasteners or adhesives to join the compliant reinforcing member to the pericardium. For instance, FIG. 5 shows the reinforcement (170) attached to the pericardium (172) variously with a surgical staple (174) and a suture (176). Other mechanical fasteners such as blind rivets (178) or the like are also suitable and within the scope of knowledge of the worker in this art.

Figure 6:
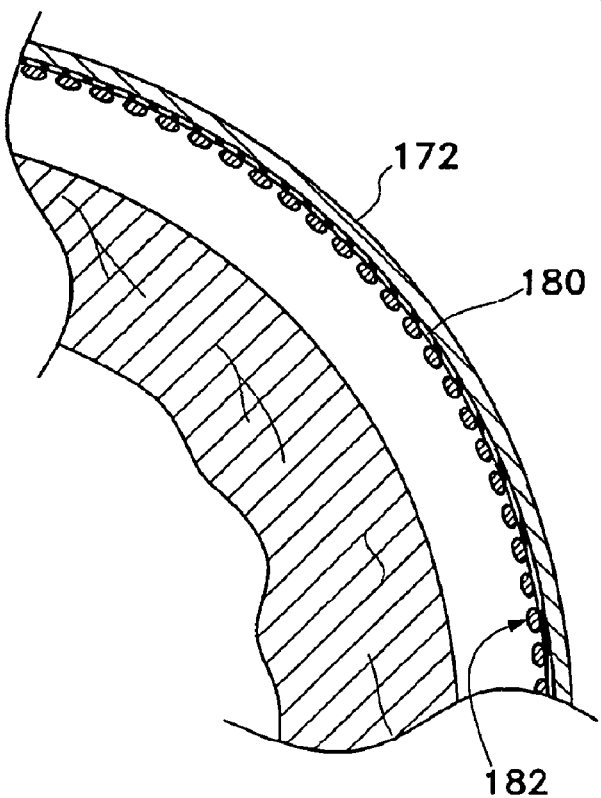

Similarly, FIG. 6 depicts the use of a biological adhesive based perhaps on fibrin or polycyanoacrylate or other similarly operating adhesives (180) to affix the reinforcing device (182) to the pericardium (172).

Having explained the generic functioning of the respective sides of the compliant reinforcing member, we turn now to a description of physical variations of the reinforcing member. They share the desirable functionality of preferably being deliverable using percutaneous delivery methods or minimally-invasive methods.

Figure 7:
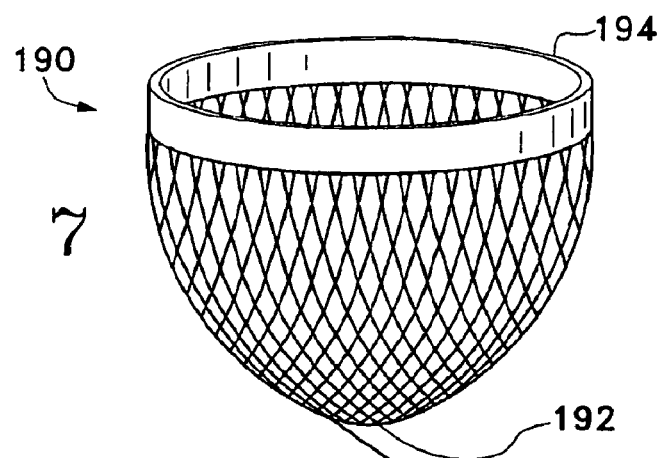
FIGS. 7, 8, and 9 show various side-views of variations of the invention.

FIG. 7 shows one such basic form (190) in which the compliant enclosure has a closed apical end (192) and an optional upper end band (194). The sack (190) may be woven or non-woven. The material used preferably has some measure of rigidity, having at least sufficient rigidity to allow an amount of pressure against the enclosing pericardium appropriate to begin the process of adherence to that pericardium. This stiffness is balanced against the need for the device (190) to be sufficiently compliant to allow passage through a cannula, or the like, during the procedure of introducing the device (190) into the pericardial sac.

A schematic introducer (196) is shown in this variation and in many of the other variations discussed herein. Typically the introducer (196) will be a wire or rod having a loop carrying the upper end of the device, e.g., band (194) in FIG. 7, during the introducing step. The loop may then be removed from the heart or may remain with the device as a stiffening member.

The variation (190) shown in FIG. 7 may be sufficiently extensive in size that it extends up to the region of the pericardium adjacent the pulmonary arteries, etc.

Figure 8:
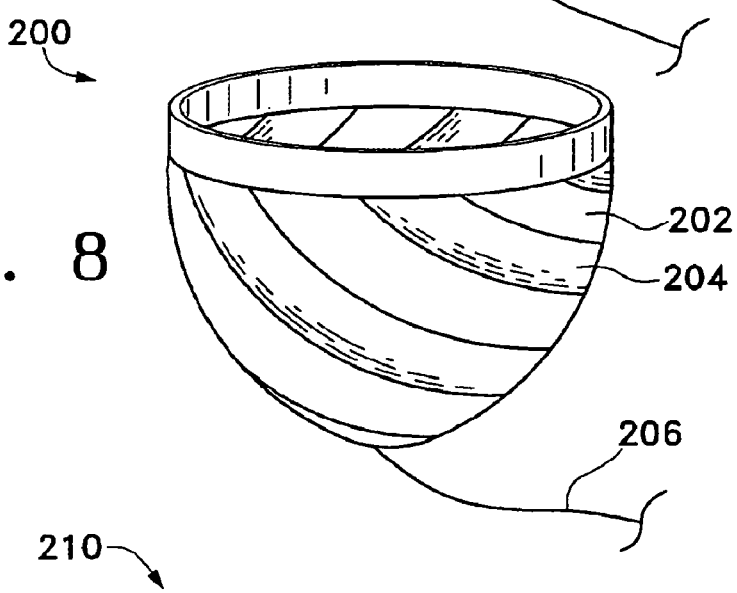

FIG. 8 shows a side view of a variation of the inventive pericardial reinforcement (200) having a generally pericardial form due to the presence of webbing (204) spaced-apart by gaps (202). Webbing (204) may be fabric, individual threads, cords, etc—many of which are discussed elsewhere herein, but desirably the webbing is formed in such a way as to allow for ease of folding and conformation during delivery of the device near and past the heart's apical end. A schematic delivery wire or introducer (206) is shown.

Figure 9:
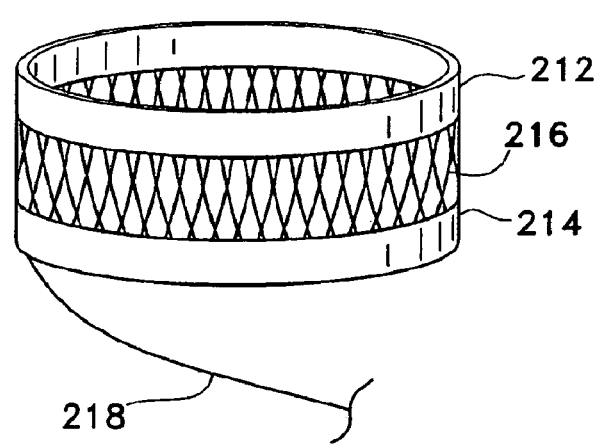

FIG. 9 shows a side view of a variation of the pericardial reinforcement device (210) that is open in the end normally near the apical end of the heart and generally is band-shaped. Optional upper band (212) and lower band (214) are included. These bands (212, 214) are to provide structure to the after more-loosely woven compliant member (216) separating them. This variation (210) is especially suitable for providing support local to the ventricular valves, a region whose reinforcement is especially effective in alienating congestive heart failure. This variation minimizes the mass of material implanted into the heart region, an often desirable result. The schematic introducer (218) is shown.

Figures 10A, 10B:
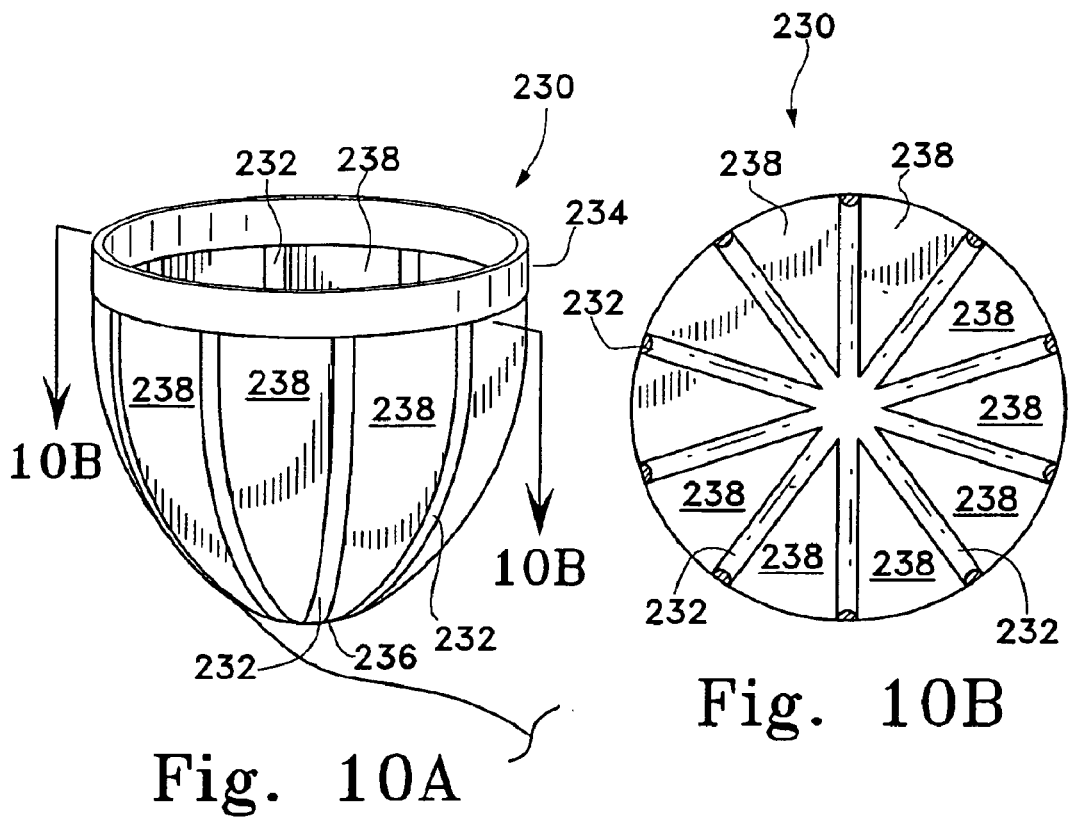
FIGS. 10A, 10B, 11A, 11B show side views (FIGS. 10A and 11A) of variations of the inventive reinforcing member and cross-sectional views (FIGS. 10B and 11B) of those variations.

FIGS. 10A and 10B show, respectively, a side view and a top cross-sectional view of another ribbed variation (230). As shown in FIG. 10A, this variation (230) includes ribs (232) that extend from an upper (but optional) band (234) to an apical end (236). As may be seen in FIG. 10B, the ribs (232) may be semicircular in cross-section. although there is a preference for the exterior of the ribs (232) to be a shape conformable to the pericardium, the cross-sectional shape of the ribs is not particularly important. The ribs (232), as shown in FIGS. 10A and 10B, may stand alone but preferably are separated and held in place by webbing (238) of any of the various forms discussed herein.

Figures 11A, 11B:
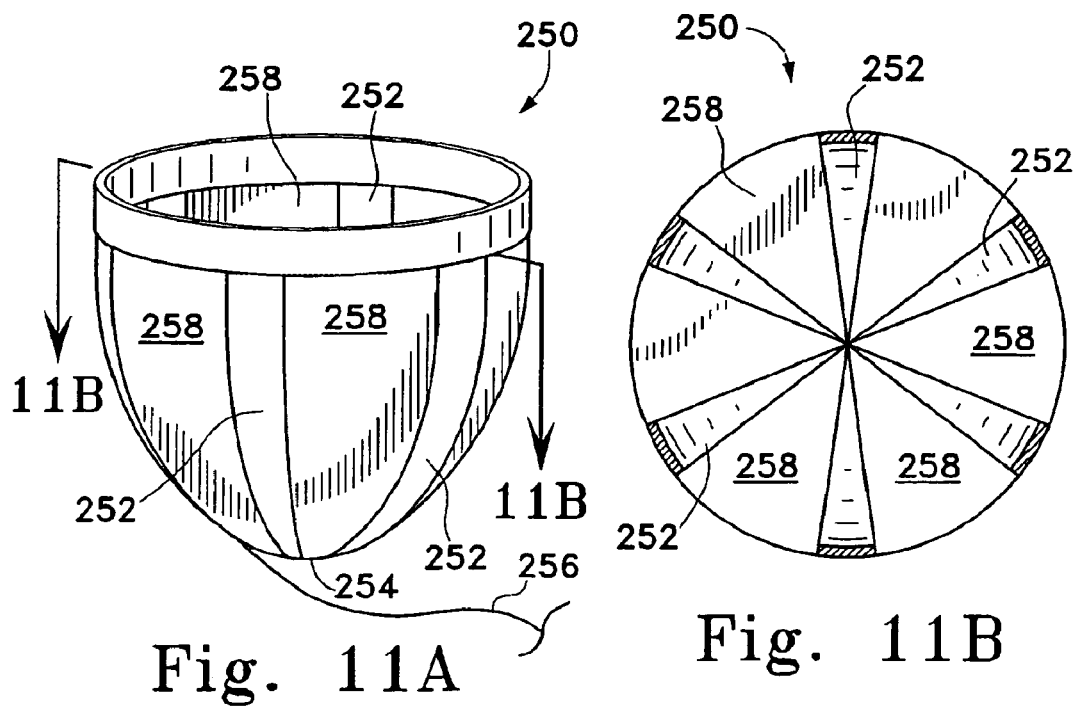

FIGS. 11A and 11B show, respectively, a side view and a cross-sectional view of another ribbed variation (250). As was noted just above, the ribs (252) are not semi-circular in cross-section but have more of a flat aspect. In this variation, the ribs extend to an apical and (254). A schematic introducer (256) is shown. The ribs (252) may be separated by webbing (258) if desired.

Figure 12:
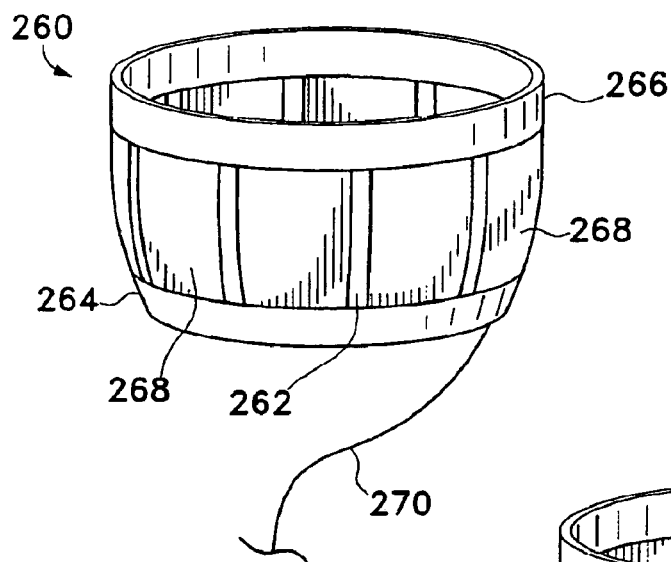
FIGS. 12, 13, and 14 show side views of variations of the invention.

FIG. 12 shows a side view of a variation (260) having ribs (262) that do not extend to the apical end, but instead stop at a lower band (264) and extend from an upper band (266). As was the case with the other variations of this type, the ribs may be separated by webbing (268). An introducer (270) is shown.

Figure 13:
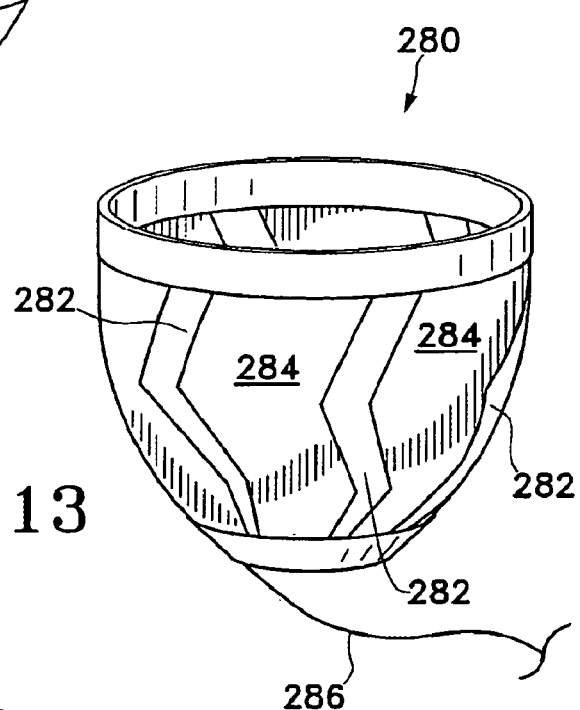

FIG. 13 shows a ribbed variation (280) of the inventive reinforcement member in which the compliant member has ribs (282) that are zig-zag in shape. This rib variation minimizes the amount of material that is introduced as rib material but distributes the stiffer reinforcing material around the periphery of the devices quite nicely. The ribs (282), again, may be separated by webbing (284) material of the type discussed elsewhere. An introducer (286) is also shown. The ribs (282) are shown to be situated "in phase" but need not be. Other convoluted forms to the ribs, e.g., sine shaped ribs, U-shaped ribs, etc., are also within the scope of the invention.

Figure 14:
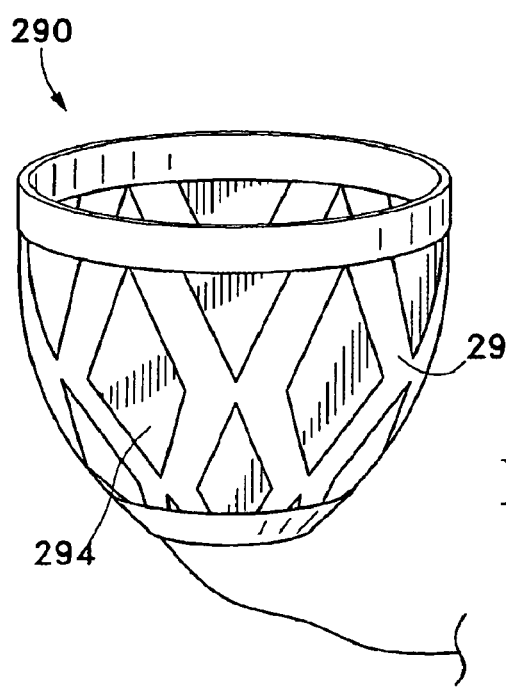

FIG. 14 shows a side view of a variation (290) of the invention where the ribs (292) are joined at their respective apexes. The ribs (292) thereby form a continuous cage about the reinforcing member (290). The various spaces (294) remaining amongst the ribs (292) may be filled with webbing if so desired.

FIGS. 15A–15D show a number of variations of the "webbing" discussed above.

Figure 15A:
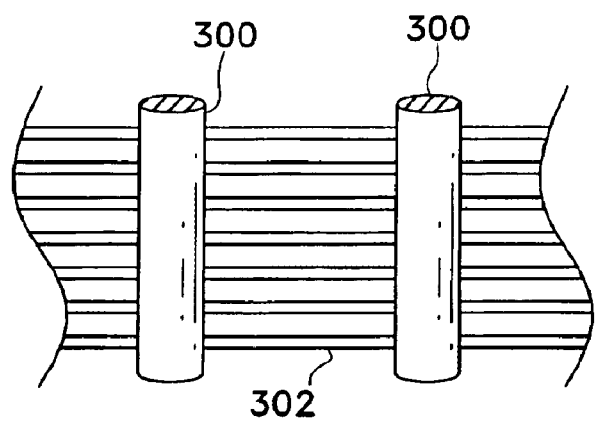
FIGS. 15A, 15B, 15C, and 15D show close-ups of various webbing variations suitable for the inventive reinforcing member.

FIG. 15A shows a number of ribs (300) separated by and held together by strands (302) of an appropriate material. The strands (302) collectively making up the webbing may be single threads or collections of threads making up a cord-like assemblage.

Figure 15B:
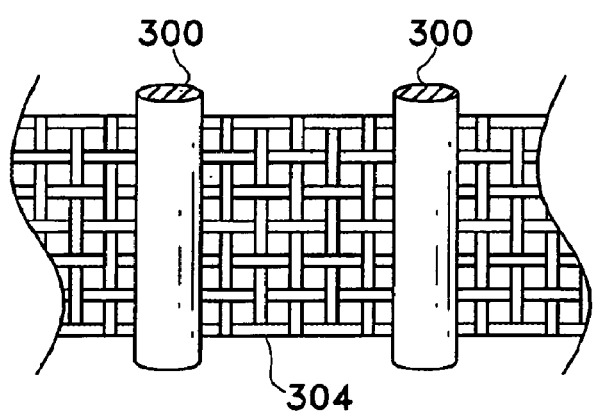

FIG. 15B shows the ribs (300) with a woven cloth (304) as the webbing material. The relative pic value may be in a range that extends between closed cloth to very open weave.

Figure 15C:
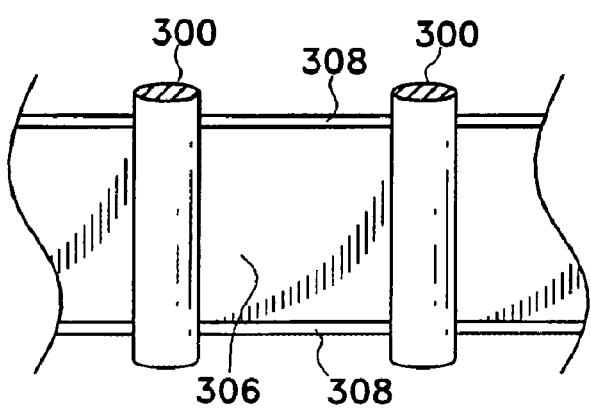

FIG. 15C shows the ribs (300) with a non-woven fabric (306) having optional upper and lower bands (308).

Figure 15D:
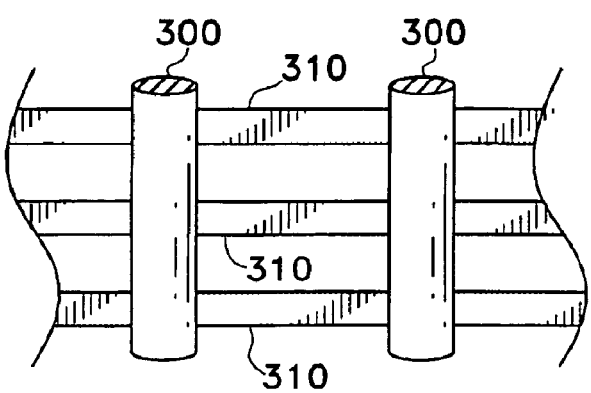

Finally, FIG. 15D shows ribs (300) separated by webbing (310) that is made up of a series of tapes (310) in turn formed from a fabric, woven or non-woven.

In addition to the generally pre-formed structures discussed above, we contemplate structures formable within the pericardial sac.

FIGS. 16A and 16B show, respectively, a side view and a cross-sectional view of a reinforcing device (320) prior to introduction into the pericardium. FIGS. 17A and 17B show, respectively, a side view and a cross-sectional view of the FIGS. 16A and 16B device after deployment.

FIG. 16A shows a side vision of a device (320) having a perforated side (322) with perforation (324). Perforations (324) communicate with inflatable lumen that is not visible in FIGS. 16A and 16B. A delivery conduit (328) is provided for introducing suitable adhesives into the device (320) in the lumen between perforated side (322) and back side (326 in FIG. 16B). Delivery conduit (328) desirably is used as an introducer for placement of the device (320) in the pericardial sac via a percutaneous or minimally invasive procedure.

The form of the device (320) shown in FIG. 16A is adapted to allow "corkscrewing" of the device as it is wound though the pericardial space. In addition, the perforated side (322) is allowed by this adaptation to migrate to the outside or pericardial side of the resulting structure. Once the proper positioning of the device (320) has been accomplished, adhesive (330) is brought into the lumen between the perforated side (322) and the opposite side (326). The adhesive flows through the perforation (324) to cause adherence between the device (320) and the surrounding pericardial wall.

Figure 18:
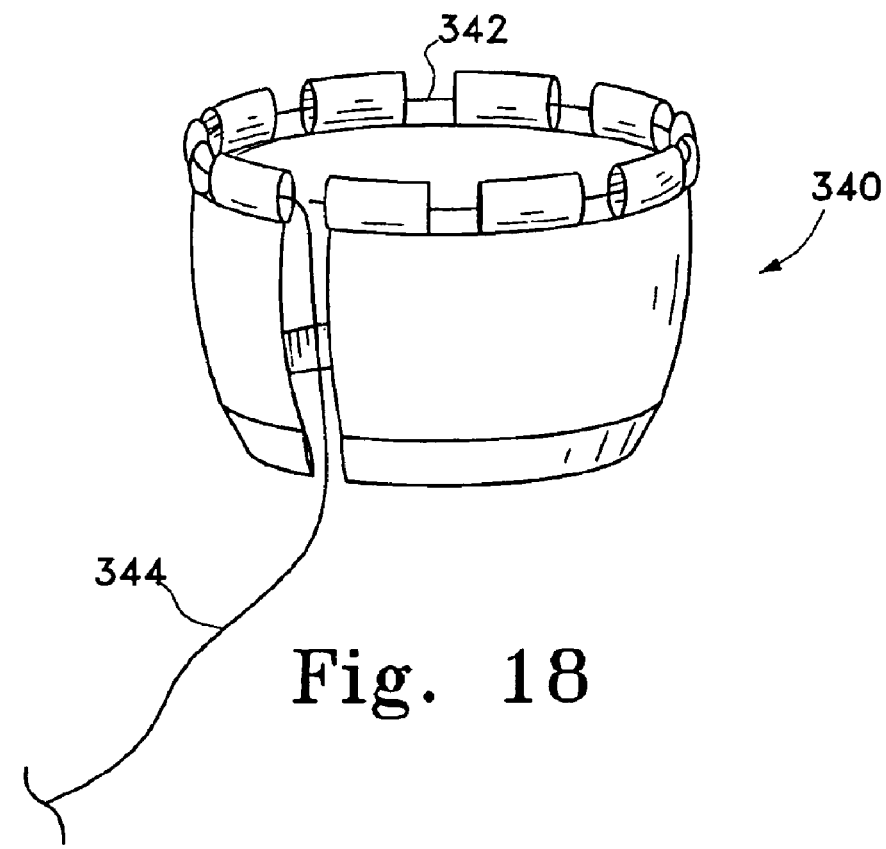
FIG. 18 shows a side view of a variation of the inventive device and an introducer.

FIG. 18 shows a variation of the reinforcing member (340) that is not a continuous band about the heart, in that it has a longitudinal opening from upper to apical end and a delivery introducer (342) that may be removed after delivery of the reinforcing member (340) to the pericardium. Optionally, the elongate section (344) of the delivery introducer (342) may be separately removed.

All of our variations are passive devices.

After a period of time, it may be desirable to alter the stiffness of the inventive reinforcing device. Because the device is preferably adherent to or ingrown with the pericardium, replacement is not a desired step. Simple size adjustment would be. FIGS. 19, 20A, 20B, and 21 show various features allowing for adjustment of some size of the installed pericardial reinforcement device.

Figure 19:
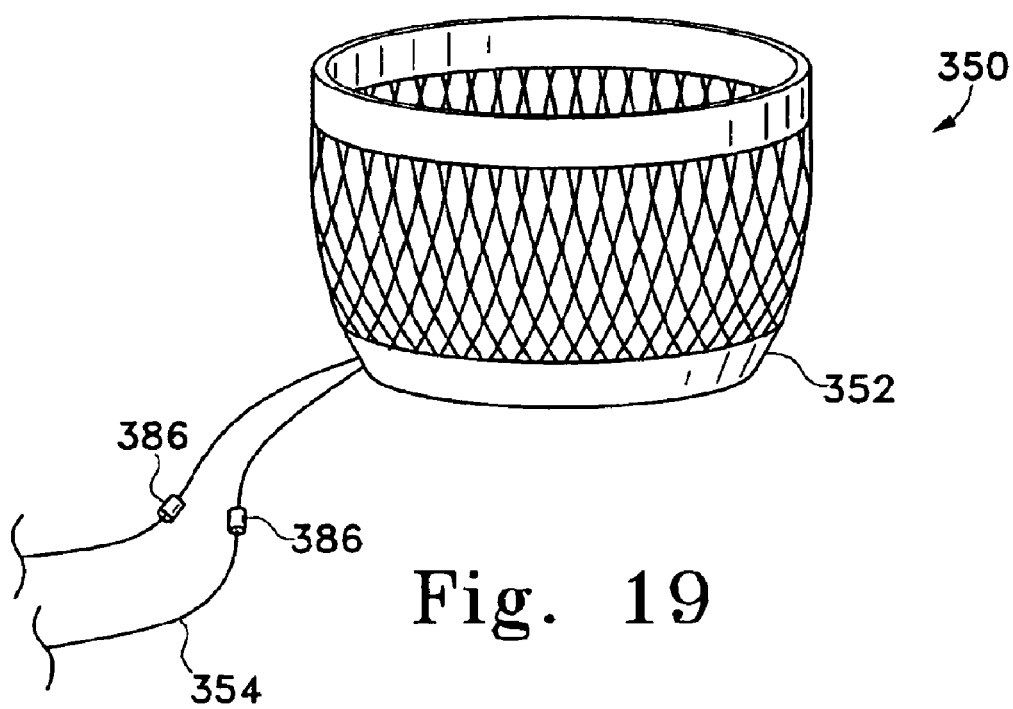
FIG. 19 shows a side view of a variation of the inventive device having a draw-string adjuster.

FIG. 19 shows a simple or generic reinforcing device (350) similar in structure and concept to that found in FIG. 9. An added feature is the structure of the lower band (352) and its attendant drawstring (354). The lower band (352) has a lumen that circumscribes the lower end of the device (350). The drawstring (354) passes through this circumscribing lumen. It is desirable to place radio-opaque markers (386), e.g., platinum or gold bands, on the drawstring (354)

to allow for later detection and manipulation. The concept is simple: to pull on the drawstring (354) either both sides together or one side against the other, thereby, to cinch the lower band into a smaller diameter. Some design thought must be had to permit the drawstring (354) to slide within the lower band (352), e.g., by proper choice of materials on this portion. Tugging on the drawstrings (354) of the heart will tighten the pericardium and provide additional firmness to that pericardium in slowing the progression of CHF. The drawstring (354) may be situated so that it is adjustable from within or without the pericardial space.

Figure 20A:
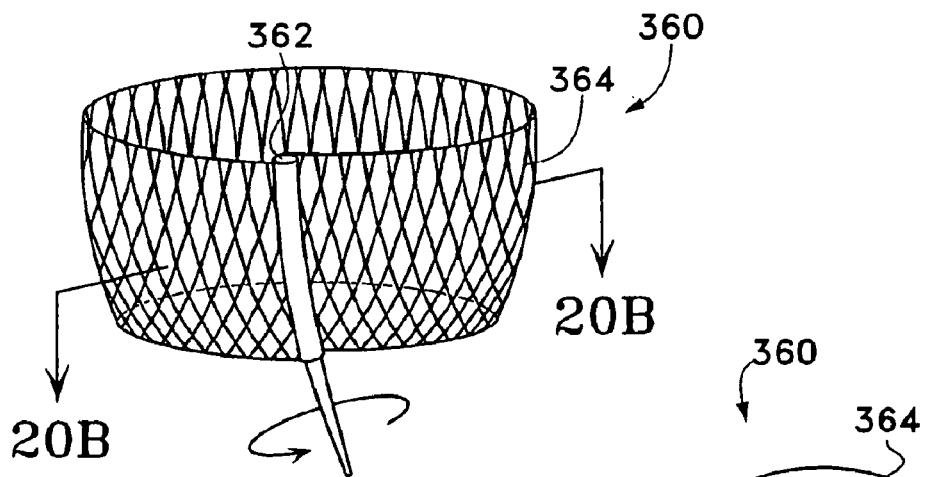
FIG. 20A shows a side view of a variation of the inventive device having a roller adjuster.
Figure 20B:
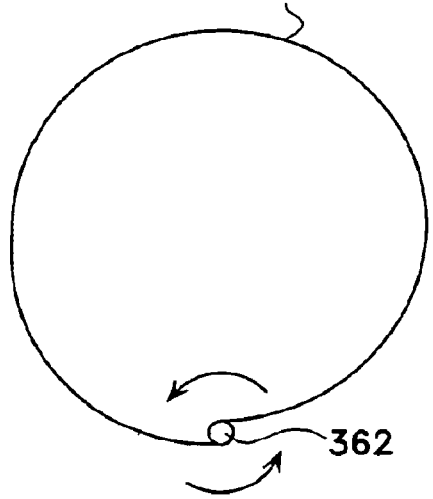
FIG. 20B shows a top view of the FIG. 20A variation schematically depicting the operation of the adjuster.

FIGS. 20A and 20B show a tightener variation in which the reinforcement device (360) includes a rotatable spine (362) that is affixed to the compliant member (364) that, in turn, is adherent to the pericardium. Twisting of the spine (362) tightens the reinforcement device and hence the pericardium. Desirably, the spine (362) may be twisted from the pericardial space near the apex of the enclosed heart.

FIG. 20B schematically shows the twisting of spine (362).

Figure 21:
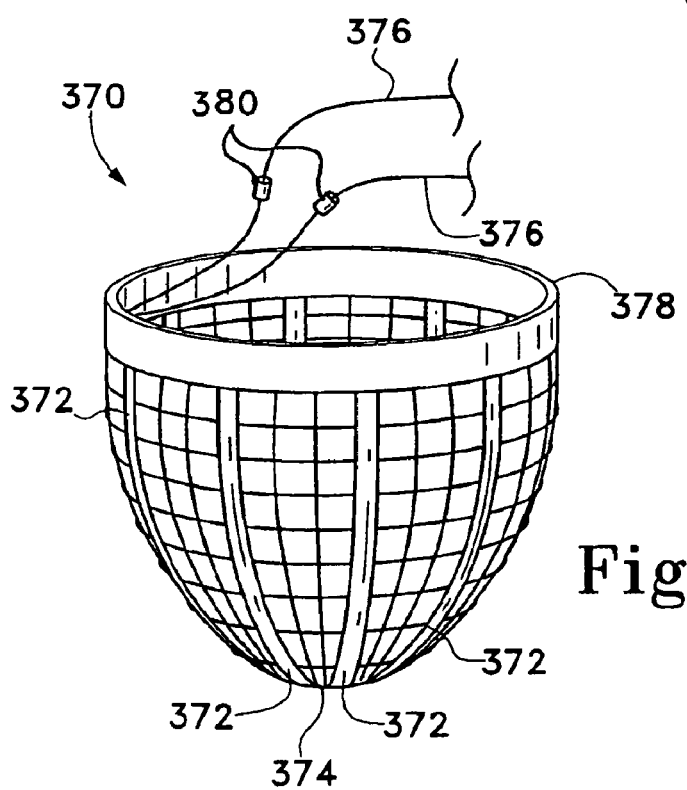
FIG. 21 shows a side view of a variation of the inventive device also having a draw-string adjuster.

FIG. 21 shows a variation (370) similar in structure to that shown in

FIGS. 10A and 10B. Each of these variations includes ribs (372 in FIGS. 21 and 232 in FIGS. 10A and 10B) that meet at an apex. The ribs (372) may be fixed together at that apex (374) or may flex freely about that lower point. In either case, the drawstring (376) in the lumen upper band (378) may be tightened to close the upper band (378) and to tighten the structure of inventive device (370). Again, use of radio-opaque markers (380) is highly desirable. The drawstring (376) should be placed so to be accessible to the pericardial space.

Several of the benefits extending from the inventive device may be summarized in the following way: Our device is intended not substantially to contact the epicardium in normal use. Consequently, many of the problems inherent simply in the act of contacting the myocardial tissue, e.g., arrhythmia, myocarditis, etc., may be minimized. Because our implant is designed not substantially to contact the epicardium, any consequent coarsening of the epicardial tissue is lessened.

The pericardium is in a gross engineering sense, a liquid-filled shock absorber that tends to exert a constant force upon the epicardium that is assessable via the fluid pressure in the pericardial space. This pressure is in some measure, related to the fitness and strength of the pericardium. Placement of implants upon the epicardial surface provides support to that surface, but the support is at the cost of direct implant contact. Our device provides the same or similar support in a much more gentle and uniform way, by supporting the pericardium and thereby supporting the fluid that supports the heart.

Additionally, sizing and placement of the pericardial reinforcement is somewhat simpler in that the object of the placement procedure is not actively beating but is only a membrane that is passively affected by the beating muscle.

One highly desirable method for placement of the inventive reinforcement is shown in FIGS. 22A–22E.

This inventive device is neat and, because it is situated in contact with the pericardium, is suitable for placement via any number of procedures, ranging from the most invasive—open chest surgery—to those that are much less invasive. A preferred procedure for placing the device is via a percutaneous approach through the diaphragm beneath the xiphoid process. The procedure is direct and uses short instruments for ease and accuracy. Such a process is outlined in FIGS. 22A–22F.

Figures 22A, 22B:
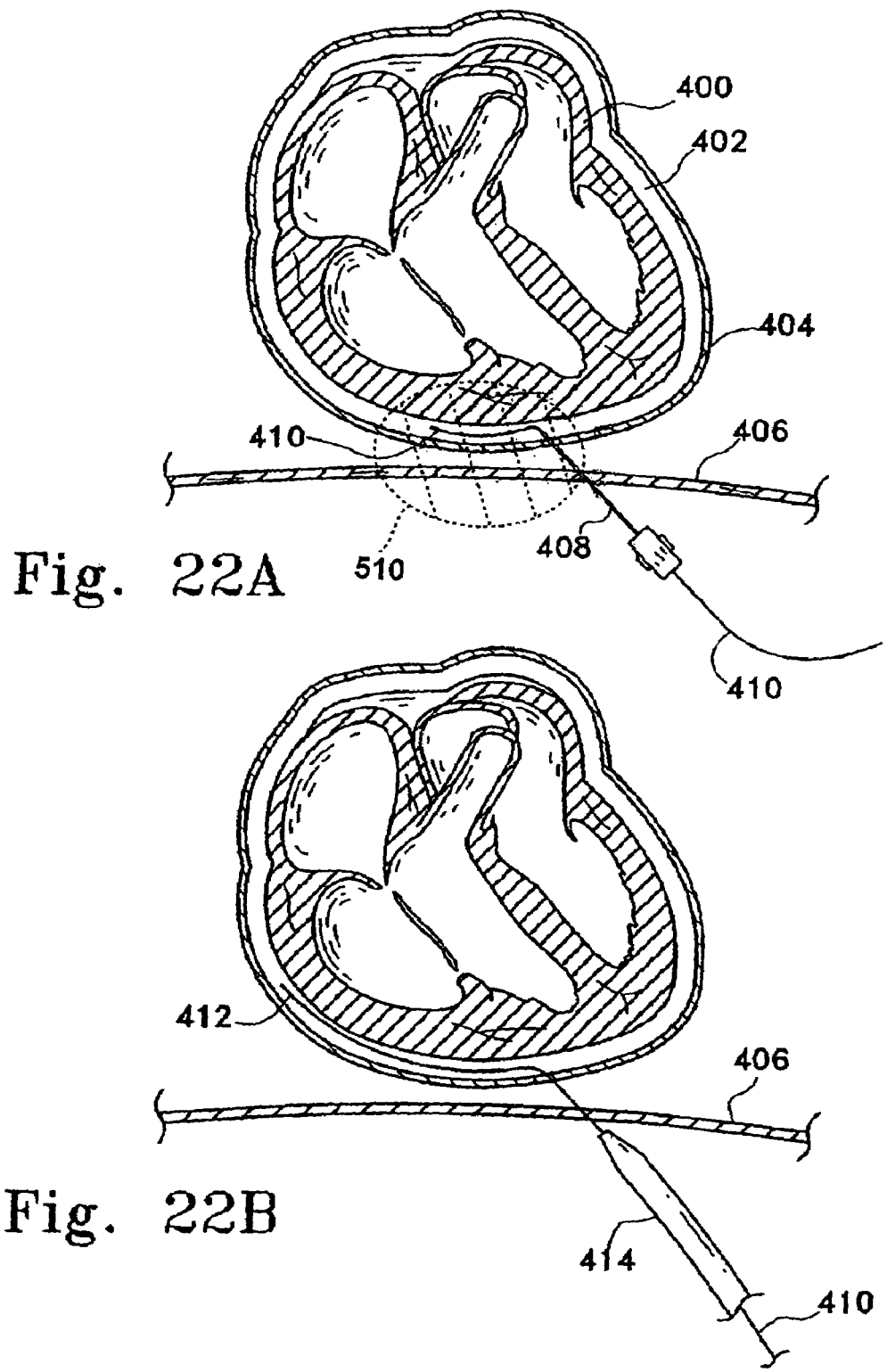
FIGS. 22A–22E show a method for introducing the inventive device into contact with the pericardium.

Shown in FIG. 22A is a heart (400) surrounded by a pericardial space (402) holding pericardial fluid and all is enclosed by the pericardium (404). Also shown is the muscle sheet known as the diaphragm (406). For the purposes of depicting the spatial relationships in this procedure, the xiphoid process (510) is shown in shadow. Much of the extraneous body structure not otherwise needed for explanation of the procedure have been omitted for clarity.

Also shown in FIG. 22A is the first step of the procedure. A suitably large hollow needle (408) and a guidewire (410) passing through the lumen of the needle (408) have been introduced below the xiphoid process and through the diaphragm (406). The needle (408) and the guidewire (410) are shown having penetrated the pericardium (404) and having passed into the pericardial space (402).

FIG. 22B shows that the needle has been removed from the guidewire (410) and the distal end (412) of the guidewire (410) has been manipulated to pass upwardly. An introducer or cannula (414) is shown being passed up the guidewire (410).

Figure 22C:
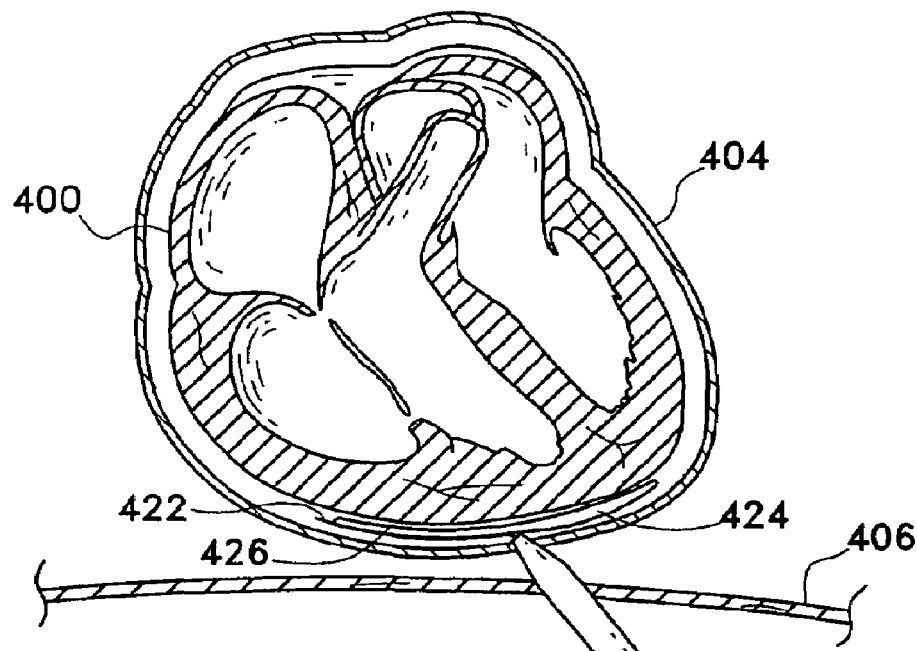

In FIG. 22C, a cannula (420) has been placed through the pericardium (404) and the introducer wire (422) has been inserted and may be seen proceeding to the left of the heart. The reinforcing device (424) begins to trail the introducer wire (422). In this variation, the upper band (426) has a relatively rigid connection with the introducer (422) and will tend to move the device about the apex of the heart (400).

Figure 22D:
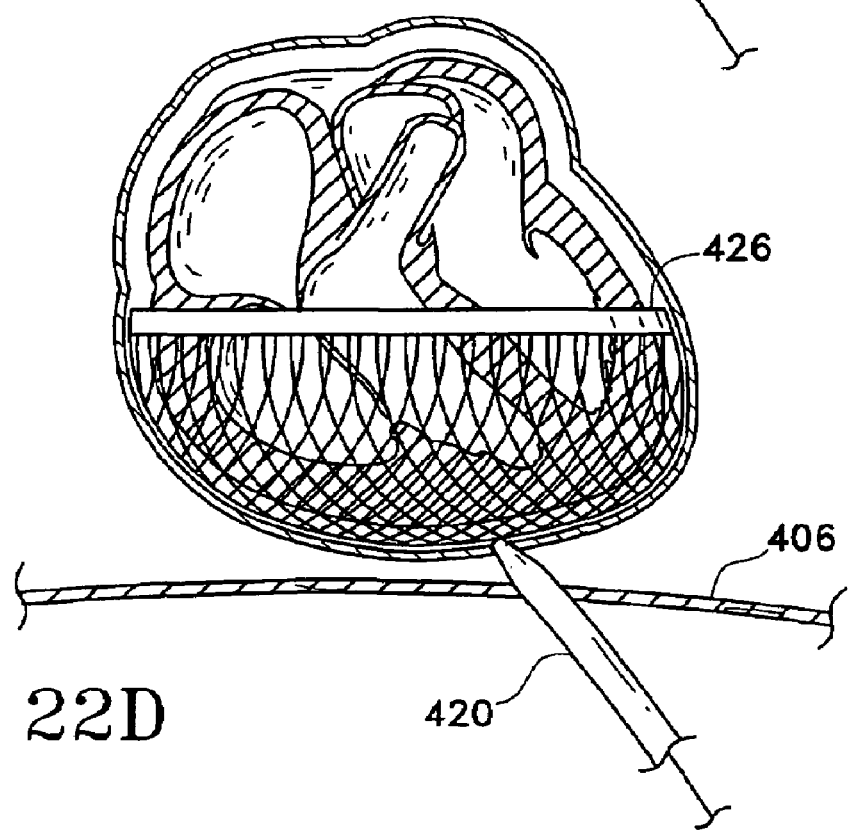

Some amount of manual manipulation will be necessary to keep the upper loop (426) following the contours of the epicardium until it reaches its desired site as shown in FIG. 22D. A vibratory or oscillatory motion may be desirable to urge the device to its final spot.

Figure 22E:
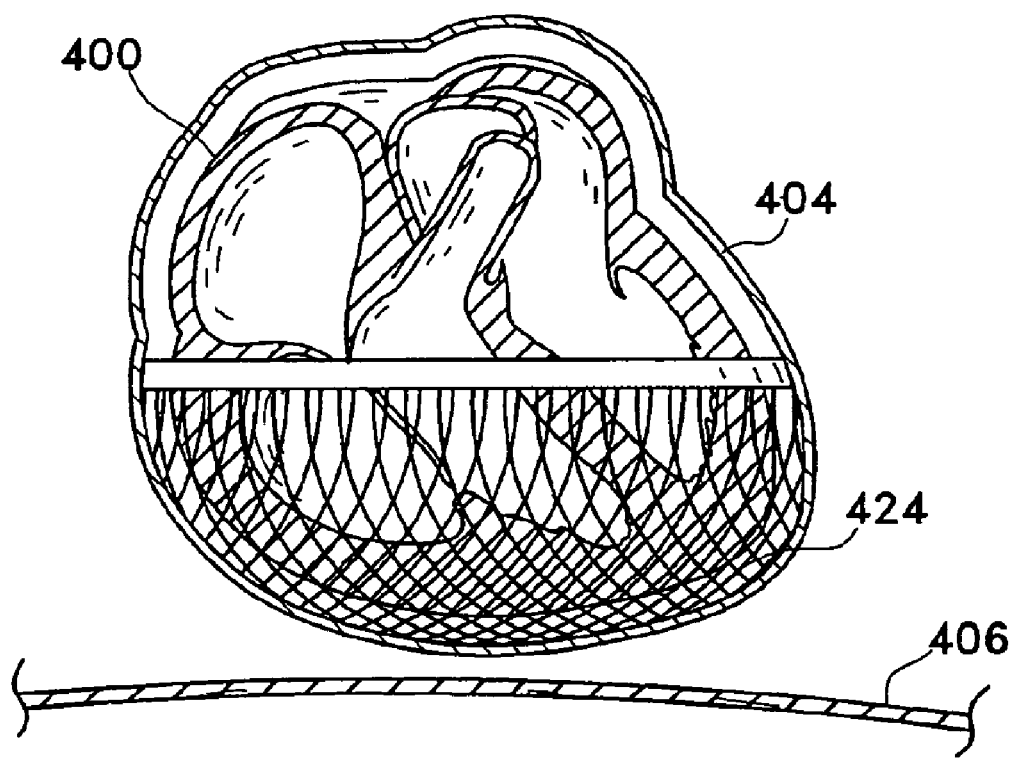

In FIG. 22E, the introducer wire (422) and cannula (420) have been removed and their access points repaired, leaving the device (424) against the pericardial membrane (404) for attachment, adherence, or ingrowth.

Many alterations and modifications may be made by those of ordinary skill in this art, without departing from the spirit and scope of this invention. The illustrated embodiments have been shown only for purposes of clarity and the examples should not be taken as limiting the invention as defined in the following claims. Which claims are intended to include all equivalents, whether now or later devised.

The invention claimed is:

1. A compliant and substantially non-elastic pericardial reinforcement comprising an enclosure generally conforming in shape to at least a portion of the heart, said enclosure consisting essentially of a compliant and substantially non-elastic member having an interior surface for placement adjacent an epicardium, the interior surface tending to inhibit adhesions with the epicardium and having an exterior surface for attachment to the interior of a pericardium, the substantially non-elastic member comprising one or more adjacent layers of material contiguous across the interior and exterior surfaces.

2. The pericardial reinforcement of claim 1 where the interior surface comprises at least one material that does not substantially permit ingrowth with said epicardium.

3. The pericardial reinforcement of claim 1 where the interior surface comprises at least one material that resists ingrowth with the epicardium.

4. The pericardial reinforcement of claim 1 where the compliant member is conformable in shape to at least a portion of the epicardium.

5. The pericardial reinforcement of claim 1 where the interior surface comprises a lubricious material.

6. The pericardial reinforcement of claim 1 where the interior surface comprises a lubricious polymeric material.

7. The pericardial reinforcement of claim 6 where the interior surface polymeric material comprises a fluorocarbon polymer.

8. The pericardial reinforcement of claim 7 where the fluorocarbon polymer is selected from the group consisting of polytetrafluoroethylene, ethylene-chiorofluoroethylene, fluorinated ethylene propylene, polychlorotrifluoroethylene, polyvinylfluoride, and polyvinylidenefluoride.

9. The pericardial reinforcement of claim 7 where the fluorocarbon polymer comprises ePTFE.

10. The pericardial reinforcement of claim 7 where the fluorocarbon polymer comprises ePTFE having internodal spacing less than about 40 microns.

11. The pericardial reinforcement of claim 6 where the polymer material comprises a member selected from the group consisting of LLDPE, LDPE, HDPE, polypropylene, polyamides, their mixtures and co-polymers.

12. The pericardial reinforcement of claim 1 where the exterior surface comprises a material for ingrowth into the pericardium.

13. The pericardial reinforcement of claim 1 where the exterior surface comprises a material allowing attachment to the pericardium.

14. The pericardial reinforcement of claim 1 where the exterior surface comprises a material for adherence with the pericardium.

15. The pericardial reinforcement of claim 1 where the exterior surface further comprises a material promoting endothelization.

16. The pericardial reinforcement of claim 15 where the material promoting endothelization comprises an effective hyaluronate salt.

17. The pericardial reinforcement of claim 15 where the material promoting endothelization comprises an effective amount of an angiogenic material.

18. The pericardial reinforcement of claim 1 where the exterior surface comprises a material enhancing ingrowth with the pericardium.

19. The pericardial reinforcement of claim 7 where the exterior surface material comprises a polymeric material.

20. The pericardial reinforcement of claim 19 where the exterior surface polymeric material is selected from the group consisting of polyethylene terephthalate, polyglycolic acid, polylactic acid, reconstituted collagen, poly-p-dioxanone, poly(glycolide-lactide) copolymer, poly(glycolide-trimethylene carbonate) copolymer, poly(glycolide-ε-caprolactone) copolymer, glycolide-trimethylene carbonate triblock copolymer, their block and random copolymers, mixtures, and alloys.

21. The pericardial reinforcement of claim 19 where the exterior surface polymeric material comprises ePTFE.

22. The pericardial reinforcement of claim 21 where the ePTFE has internodal spacing greater than about 60 microns.

23. The pericardial reinforcement of claim 1 where the exterior surface material comprises a woven or non-woven polymeric material.

24. The pericardial reinforcement of claim 23 where the exterior surface material comprises a woven polymeric material.

25. The pericardial reinforcement of claim 23 where the exterior surface material comprises a non-woven polymeric material.

26. The pericardial reinforcement of claim 1 further comprising at least one mechanical linkage configured to attach the exterior surface to the pericardium.

27. The pericardial reinforcement of claim 26 where the at least one mechanical linkage comprises at least one suture.

28. The pericardial reinforcement of claim 26 where the at least one mechanical linkage comprises at least one staple.

29. The pericardial reinforcement of claim 26 where the at least one mechanical linkage comprises a material selected from the group consisting of adhesives and glues.

30. The pericardial reinforcement of claim 29 where the adhesives and glues are selected from the group consisting of acrylate-based glues, cyanoacrylate-based glues, and fibrin-based glues.

31. The pericardial reinforcement of claim 30 where the at least one mechanical linkage comprises an acrylate-based glue.

32. The pericardial reinforcement of claim 30 where the at least one mechanical linkage comprises a cyanoacrylate-based glue.

33. The pericardial reinforcement of claim 30 where the at least one mechanical linkage comprises a fibrin-based glue.

34. The pericardial reinforcement of claim 1 where the exterior surface is textured for ingrowth into the pericardium.

35. The pericardial reinforcement of claim 1 where the compliant and substantially non-elastic member comprises an inner member layer and an outer member layer.

36. The pericardial reinforcement of claim 35 where at least one of the inner layer and the outer layer comprises a woven fabric.

37. The pericardial reinforcement of claim 35 where at least one of the inner layer and the outer layer comprises a non-woven fabric.

38. The pericardial reinforcement of claim 35 where the inner layer and the outer layer comprise separate layers of woven or non-woven fabric.

39. The pericardial reinforcement of claim 35 where the inner layer is laminated to the outer layer.

40. The pericardial reinforcement of claim 35 where at least one of the inner layer and the outer layer is substantially non-porous.

41. The pericardial reinforcement of claim 35 where at least one of the inner layer and the outer layer is non-continuous.

42. The pericardial reinforcement of claim 1 further comprising an adjuster adapted for changing a compliant and substantially non-elastic member size after attachment of that member to the interior of the pericardium.

43. The pericardial reinforcement of claim 42 where the adjuster comprises a rotatable roller.

44. The pericardial reinforcement of claim 42 where the adjuster comprises a drawstring.

45. The pericardial reinforcement of claim 1 where the compliant and substantially non-elastic member comprises a band.

46. The pericardial reinforcement of claim 1 where the compliant and substantially non-elastic member comprises a band having an upper end and an apical end and a length extending from the upper end to the apical end and where the length of the band is less than about ⅓ length of a heart to which it is applied.

47. The pericardial reinforcement of claim 46 where the band has a length substantially matching the width of an A–V groove on a heart to which it is applied.

48. The pericardial reinforcement of claim 1 where the compliant and substantially non-elastic member comprises a sack having a closed end.

49. The pericardial reinforcement of claim 48 where the compliant and substantially non-elastic member comprises a sack having a closed end and sized to be positioned only along and less than about ⅓ length of an apical end of heart to which it is applied.

50. The pericardial reinforcement of claim 1 where the compliant and substantially non-elastic member comprises a substantially elongated member having a distal end and a proximal end and is configured to be helical upon introduction into the region of the pericardium.

51. The pericardial reinforcement of claim 50 where the compliant and substantially non-elastic member comprises a substantially elongated member having a lumen extending from the proximal end at least partially to the distal end.

52. The pericardial reinforcement of claim 51 where the substantially elongated member includes at least one orifice open to the exterior surface when the device is helically configured in the region of the pericardium.

53. The pericardial reinforcement of claim 52 further comprising a source of glue or adhesive flowable through the at least one orifice, the glue or adhesive suitable for causing adherence between the compliant member and the pericardium.

54. The pericardial reinforcement of claim 53 where the substantially elongated member is expandable upon introduction of the glue or adhesive into the lumen.

55. The pericardial reinforcement of claim 1 further comprising at least one rib found over the enclosure.

56. The pericardial reinforcement of claim 1 where the compliant and substantially non-elastic member comprises a band having an upper end and an apical end and a length extending from the upper end to the apical end and having at least two open, generally opposing openings.

57. The pericardial reinforcement of claim 56 where the band has a length less than about ⅓ length of a heart to which it is applied.

58. The pericardial reinforcement of claim 55 where the at least one rib has a flexibility different than a flexibility of the compliant and substantially non-elastic member.

59. The pericardial reinforcement of claim 55 where the at least one rib comprises a generally helical member.

60. The pericardial reinforcement of claim 59 where the generally helical member comprises a ribbon-like member.

61. The pericardial reinforcement of claim 55 where each at least one rib comprises a ribbon-like member.

62. The pericardial reinforcement of claim 61 where each ribbon-like member has a width-thickness ratio greater than about two.

63. The pericardial reinforcement of claim 62 where each ribbon-like member has a width-thickness ratio greater than about seven.

64. The pericardial reinforcement of claim 59 where the generally helical member is inflatable over at least a portion of the enclosure.

65. The pericardial reinforcement of claim 59 where the generally helical member is incrementally inflatable.

66. The pericardial reinforcement of claim 55 where the compliant and substantially non-elastic member comprises an enclosure generally conforming in shape to at least a portion of an pericardium and having an upper end and an apical end and a length extending from the upper end to the apical end and having multiple ribs extending from the upper end to the apical end.

67. The pericardial reinforcement of claim 66 where the multiple ribs are each ribbon-like.

68. The pericardial reinforcement of claim 67 where each ribbon-like member has a cross section with a width-thickness ratio greater than about two.

69. The pericardial reinforcement of claim 68 where each ribbon-like member has a cross section with a width-thickness ratio greater than about seven.

70. The pericardial reinforcement of claim 66 where the multiple ribs each have a round cross section.

71. The pericardial reinforcement of claim 66 where the multiple ribs each have a cross section with a width-thickness ratio of two or less.

72. The pericardial reinforcement of claim 66 where the multiple ribs are each zigzag in shape.

73. The pericardial reinforcement of claim 72 where the multiple zigzag ribs have substantially adjacent points and at least some of the adjacent points are connected.

74. The pericardial reinforcement of claim 66 where at least some of the multiple ribs are joined at the apical end.

75. The pericardial reinforcement of claim 66 where the enclosure comprises a woven fabric.

76. The pericardial reinforcement of claim 75 where the fabric comprises an open weave fabric.

77. The pericardial reinforcement of claim 66 where the enclosure comprises one or more ribbons extending between at least some of the multiple ribs.

78. The pericardial reinforcement of claim 66 where the enclosure comprises one or more fibers extending between at least some of the multiple ribs.

79. The pericardial reinforcement of claim 66 where the enclosure comprises an elastic material.

80. The pericardial reinforcement of claim 66 where the enclosure comprises a substantially inelastic material.

81. The pericardial reinforcement of claim 66 where the enclosure has a longitudinal opening extending from the upper end towards the apical end and including a plurality of looping members situated on said upper end, said loops deployable over a looping deployment tool.

82. The pericardial reinforcement of claim 81 further including a looping deployment tool, the tool adapted to be removable after placement of the compliant and substantially non-elastic member adjacent said pericardium.

83. The pericardial reinforcement of claim 82 where the looping deployment tool further comprises a connector member for separable connection to an installation member.

84. The pericardial reinforcement of claim 83 where the looping deployment tool further comprises the installation member.

85. The pericardial reinforcement of claim 66 where the compliant and substantially non-elastic member further comprises a connector member for separable connection to an installation member.

86. The pericardial reinforcement of claim 85 where the compliant and substantially non-elastic member further comprises the installation member.

87. A method for reinforcing the pericardium comprising the steps of:
   a) introducing the pericardial reinforcement of claim 1 proximate a xiphoid process through a pericardium wall into a pericardial space, and
   b) positioning the pericardial reinforcement adjacent the pericardium.

88. The method of claim 87 further comprising the steps of puncturing skin beneath the xiphoid process with a needle and an introducer and passing the needle and introducer through the pericardium to the pericardial space.

89. The method of claim 88 further comprising the steps of withdrawing the needle and introducing a guidewire and a cannula through the introducer.

90. The method of claim 87 further comprising the subsequent step of tightening the pericardial reinforcement.

* * * * *